(12) United States Patent
Bitterlich et al.

(10) Patent No.: US 7,749,414 B2
(45) Date of Patent: Jul. 6, 2010

(54) COMPOSITE MEMBRANE

(75) Inventors: Stefan Bitterlich, Dirmstein (DE); Hartwig Voβ, Frankenthal (DE); Gunter Schuch, Ludwigshafen (DE); Armin Diefenbacher, Germersheim (DE); Manfred Noack, Berlin (DE); Ronald Schäfer, Aalen (DE); Ingolf Voigt, Jena (DE); Hannes Richter, Hermsdorf (DE); Jürgen Caro, Berlin (DE)

(73) Assignee: BASF AG (DE)

( * ) Notice: Subject to any disclaimer, the term of this patent is extended or adjusted under 35 U.S.C. 154(b) by 1010 days.

(21) Appl. No.: 10/585,703

(22) PCT Filed: Jan. 5, 2005

(86) PCT No.: PCT/EP2005/000047

§ 371 (c)(1),
(2), (4) Date: Jul. 11, 2006

(87) PCT Pub. No.: WO2005/068057

PCT Pub. Date: Jul. 28, 2005

(65) Prior Publication Data

US 2007/0137485 A1    Jun. 21, 2007

(30) Foreign Application Priority Data

Jan. 13, 2004    (DE) ................. 10 2004 001 974

(51) Int. Cl.
*B29C 44/04* (2006.01)
*B01D 39/14* (2006.01)
*B01D 39/06* (2006.01)

(52) U.S. Cl. .............. 264/45.1; 210/500.25; 210/490; 55/523; 55/524; 264/652

(58) Field of Classification Search .............. 210/500.9, 210/500.25, 640; 95/45–52; 55/523, 524; 264/45.1, 652; 428/426
See application file for complete search history.

(56) References Cited

U.S. PATENT DOCUMENTS

| | | | |
|---|---|---|---|
| 4,699,892 A | 10/1987 | Suzuki | |
| 5,019,263 A | 5/1991 | Haag et al. | |
| 6,197,427 B1 * | 3/2001 | Anstett et al. | 428/426 |
| 7,252,876 B2 * | 8/2007 | Mori et al. | 428/312.2 |
| 7,357,836 B2 * | 4/2008 | Tsapatsis et al. | 117/68 |
| 7,476,635 B2 * | 1/2009 | Chau et al. | 502/4 |

FOREIGN PATENT DOCUMENTS

| | | |
|---|---|---|
| EP | 0 180 200 | 5/1986 |
| EP | 0 460 512 | 12/1991 |
| GB | 2 340 112 | 2/2000 |
| WO | WO-94/01209 | 1/1994 |
| WO | WO-94/25151 | 11/1994 |

OTHER PUBLICATIONS

Paravar, A. et al., "Direct Measurement of Diffusivity for Butane Across a Single Large Silicalite Crystal", from Proc. 6th Int. Zeolite Conference, Reno, USA, 1983, Eds. D. Olson et al., 1984, pp. 217-224.

* cited by examiner

*Primary Examiner*—Ana M Fortuna
(74) *Attorney, Agent, or Firm*—Connolly Bove Lodge & Hutz LLP

(57) ABSTRACT

Composite membranes comprising at least one porous substrate layer and at least one microporous separation layer, comprising at least one zeolite of the MFI type, are described, the separation layer being produced by a hydrothermal synthesis in which the molar ratio of silicon to aluminum is greater than 120 and the separation layer contains less than 10% by weight of aluminum in elemental or chemically bound form in a zone of at least 100 nm adjacent to the separation layer.

3 Claims, No Drawings

COMPOSITE MEMBRANE

RELATED APPLICATIONS

This application is a national stage application (under 35 U.S.C. 371) of PCT/EP2005/000047 filed Jan. 5, 2005, which claims benefit to German application 10 2004 001 974.6 filed Jan. 13, 2004.

The present invention relates to a composite membrane which contains at least one porous substrate and at least one microporous separation layer, the separation layer containing a zeolite of the MFI type. The present invention furthermore relates to a process for the production of these composite membranes and a process for separating olefins, in which the novel composite membranes are used.

In chemical and petrochemical production processes, it is frequently necessary to separate olefin-containing mixtures. In general, the separation can be performed sufficiently well by distillation processes. However, in the case of mixtures having a very narrow boiling range, distillative working-up which can be carried out in an economical manner is possible, if at all, only with the use of assistants which necessitate additional process steps. An example of the separation of mixtures having a narrow boiling range is the separation of isomeric olefins having the same number of carbon atoms.

The literature describes articles in the separation of such mixtures by means of a membrane process, the processes generally being carried out in such a way that a material stream (feed) to be separated is separated in a selectively acting membrane and is separated into a permeate, i.e. a material stream passing through the membrane, and a retentate, i.e. a material stream which does not pass through the membrane.

A separation of linear and branched hydrocarbon isomers by means of organic membranes which takes place on the basis of the different stearic requirements of the isomeric molecules is in principle possible and is described, for example, in NEFTEKHIMIYA V23 N.4, pages 435 to 453. However, the organic membranes used in this process have the disadvantage of greatly limited thermal and chemical stability.

EP 0 180 200 A describes the selective separation of n-paraffins and n-olefins from a naphtha distillate through a ceramic membrane which consists of CaA zeolites contained in the pores of a porous $Al_2O_3$ tube.

Proc. 6th. Int. Zeolite Conference, Reno, USA, 1983, Eds. D. Olson, A. Bisio, Butterworth, London, 1984, pages 217 to 224 describes separation of n-butane and isobutane by means of a membrane comprising single crystals of the zeolite silicalite, embedded in a polymer matrix.

U.S. Pat. No. 4,699,892 describes the separation of 1-butene from a $C_4$-hydrocarbon through a CaA membrane.

WO 94/25151 and WO 94/01209 describe the production of composite membranes, i.e. membranes in which the actual layer having separation activity is applied from a zeolite of the MFI type on a macroporous substrate, by an in situ hydrothermal synthesis. The membranes which result therefrom and are used for separating n-butane/isobutane mixtures are purely ceramic membranes and have high chemical and thermal stability. However, they generally also have a high catalytic activity which, in the case of mixtures containing olefins, is generally undesired since the catalytic activity leads to the loss of useful components of the mixture to be separated or to the formation of undesired reaction products. For example, in the case of 1-butene- and/or isobutene-containing mixtures, as generally known, 2-butenes can form from 1-butene by isomerization, and dimeric and oligomeric products from isobutene, at reactive centers contained in zeolites.

U.S. Pat. No. 5,019,263 states that, in the case of a non-composite zeolite membrane, i.e. a membrane which consists only of the zeolite separation layer, the catalytic activity can be reduced by introducing alkali metal or alkaline earth metal ions into the membrane. However, noncomposite membranes have the disadvantage that, in order to ensure sufficient mechanical stability for technical use, the separation layer must have a considerable thickness, which, under given conditions, results in the transmembrane flow density being substantially lower than in the case of a composite membrane in which the thickness of the separation layer is typically in the region of a few μm.

It is an object of the present invention to provide composite membranes which have substantially no catalytic activity and have a sufficiently high mechanical stability.

We have found that this object is achieved, according to the invention, by composite membranes comprising at least one porous substrate and at least one microporous separation layer, which contain at least one zeolite of the MFI type.

In the novel composite membranes, the separation layer is produced by a hydrothermal synthesis in which the molar ratio of silicon to aluminum in the synthesis solution is greater than 120, preferably greater than 200, particularly preferably greater than 300, and the substrate contains less than 10, particularly preferably less than 5, in particular less than 1, % by weight of aluminum in elemental or chemically bound form in a zone of at least 100 nm, particularly preferably at least 250 nm, in particular at least 500 nm, adjacent to the separation layer, and the molar ratio of silicon to aluminum in the separation layer is greater than 120, particularly preferably greater than 200, in particular greater than 300.

Suitable substrates for the novel composite membranes are bodies having penetrating pores having pore diameters of 0.5 nm to 3 μm, particularly preferably from 1 to 60 nm, in particular from 5 to 60 nm. These bodies may have, for example, the form of flat disks, tubes or capillaries.

Other advantageously used substrates are multichannel elements, as used in ceramic membranes for micro- or ultrafiltration.

Depending on the above-described geometric shape of the substrate, an asymmetric structure of the substrate material is advantageous, in which said substrate consists of a plurality of successive layers having a decreasing pore diameter, the smallest pore diameter being present on that side of the substrate which is to be provided with the separation layer.

The smallest pore diameter of the substrate is preferably from 0.5 to 100 nm, particularly preferably from 0.75 to 80 nm, in particular from 1 to 60 nm.

A large number of materials, for example sintered metals, steels or oxide ceramic materials, e.g. alumina, titanium dioxide or mixtures of metal oxides consisting predominantly of titanium dioxide, are suitable as materials for the substrate. Furthermore, silica, zirconium dioxide, magnesium oxide or other metal oxides are suitable, provided that they have a low solubility under hydrothermal conditions in the synthesis solution, i.e. at a pH of from 11 to 12, a temperature of from 170 to 190° C., a pressure of from 10 to 16 bar and a concentration of less than 1 mg/l.

For the novel membranes, it is important that the molar ratio silicon to aluminum in the separation layer is greater than 120, particularly preferably greater than 200, in particular greater than 300. This ratio ensures that the number of acidic or ionic sites in the separation layer of the novel membrane is small. Consequently, isomerization or byproduct formation during a separation of isomeric olefins is reduced or even avoided.

In order to achieve the abovementioned range of the molar silicon/aluminum ratio, it is preferable if a very low-aluminum material is used as substrate material. In a preferred embodiment, the entire substrate therefore consists of one or more materials which have a low aluminum content, i.e. contain less than 1, particularly preferably less than 0.1, in particular less than 0.01, % by weight of aluminum (in the sense of elemental or chemically bound aluminum).

In the parts in which the membrane arising from it comes into contact with a sealing material, the substrate should preferably be provided with a suitable auxiliary layer, particularly preferably with a gas-tight and alkali-resistant glass solder known per se.

In a preferred embodiment of the novel composite membranes, the separation layer is such that, in a permeation measurement with an equimolar 1-butene/isobutene mixture which is carried out at a feed pressure of from 1 to 100, particularly preferably from 2 to 35, in particular from 5 to 30, bar (abs), a permeate pressure of from 0.001 to 10, particularly preferably from 1 to 10, in particular from 4 to 8, bar (a), which is below the feed pressure, a temperature of from 50 to 200° C., particularly preferably from 50 to 150° C., in particular from 50 to 130° C. and a cut (amount of permeate/amount of feed) of less than 0.1, particularly preferably less than 0.05, in particular less than 0.01, the 1-butene concentration permeate is greater than 60%, particularly preferably greater than 70%, in particular greater than 80%.

The separation layer preferably consists of MFI zeolite, particularly preferably silicalite.

The present invention furthermore relates to a process for the production of the above-described composite membranes, which comprises the following process steps:

(a) hydrothermal synthesis of a synthesis solution on a substrate by bringing the substrate into contact with the synthesis solution over a period of from 1 to 100, preferably from 5 to 50, particularly preferably from 10 to 20, hours at from 100 to 250° C., preferably from 140 to 210° C., particularly preferably from 170 to 190° C., (b) washing of the membrane resulting from process step (a) with water or an acidic solution for a period of 5 to 120, preferably from 10 to 90, minutes, (c) drying of the membrane at from 5 to 40° C., preferably from 15 to 35° C., particularly preferably from 20 to 30° C., over a period of from 1 to 100, preferably from 10 to 30, particularly preferably from 10 to 15, hours in the presence of a flowing or stationary gas, (d) calcination of the membrane at a heating rate of from 0.1 to 1, preferably from 0.1 to 0.8, particularly preferably from 0.1 to 0.75, K/min up to a temperature of from 200 to 600° C., preferably from 350 to 500° C., particularly preferably from 400 to 500° C., the residence at the final temperature being effected for from 30 to 500, preferably from 300 to 450, particularly preferably from 360 to 400, minutes and subsequently cooling being effected at a rate of from 0.1 to 10, preferably from 0.5 to 3, particularly preferably from 0.3 to 1, K/min.

In a preferred embodiment of the present invention, the process steps are carried out in the sequence (a), (b), (c) and (d).

In a particularly preferred embodiment of the novel process, the substrate material used in process step (a) is subjected, before hydrothermal synthesis, to a seeding step in which a layer of seed particles which at least partly covers that side of the substrate which is to be coated is applied to said side, and only thereafter is the hydrothermal synthesis described carried out.

The seed particles can preferably be amorphous or crystalline bodies having particle sizes of from 1 to 1000 nm, particularly preferably from 10 to 100 nm, in particular from 50 to 80 nm, which correspond in their chemical composition substantially to the separation layer to be synthesized. In a particularly preferred variant, the seed particles consist of silicalite.

The preparation of the seed particles is effected by a separate hydrothermal process. The synthesis solution used thereby preferably contains silica, sodium oxide, tetrapropylammonium hydroxide, tetrapropylammonium bromide, ethanol and water. The synthesis solution for the preparation of the seed particles contains, in each case independently of one another, preferably the abovementioned components in the following molar ratio:

1.0 of tetraethyl orthosilicate TEOS from 0 to 0.01, particularly preferably from 0 to 0.006, of sodium oxide $Na_2O$ from 0.2 to 0.5, particularly preferably from 0.3 to 0.5, in particular from 0.3 to 0.36, of tetrapropylammonium hydroxide TPAOH from 10 to 20, particularly preferably from 12 to 15, of water.

Tetrapropylammonium hydroxide can be partly or completely exchanged for tetrapropylammonium bromide if at the same time an equimolar increase in the NaOH fraction is effected.

With the use of tetraethyl orthosilicate (TEOS) as a silicon source, 4 mol of ethanol form, and 2 mol of water are consumed per mol of tetraethyl orthosilicate (TEOS).

The seed synthesis is preferably effected substantially in the absence of aluminum, i.e. the synthesis solution for the preparation of the seeds is characterized by a molar Si/Al ratio of, preferably, greater than 120, particularly preferably greater than 200, in particular greater than 300.

Said tetrapropylammonium salts in the synthesis solution for the preparation of the seed layer serve as structure-imparting agents (templates). However, it is also possible to use other templates apart from tetrapropylammonium salts, for example 1,6-hexanediol and/or piperazine. A detailed description in this context is to be found in: R. Szostak, Handbook of Molecular Sieves, page 521.

The synthesis solution for the preparation of the seed particles is preferably slowly stirred or left to stand over a period of, preferably, from 10 to 500, particularly preferably from 50 to 200, in particular from 70 to 120, hours at, preferably, from 60 to 100° C., particularly preferably from 60 to 90° C. The further processing of the suspension is preferably effected by dilution with demineralized water or by removing the solid by centrifuging, washing several times and then redispersing in demineralized water.

The demineralized water which is used for the redispersing is preferably brought to a pH of from 8 to 12, particularly preferably from 8 to 9. For example, sodium hydroxide solution or ammonia water can be used for this purpose.

Application of the seed particles to the substrate can be effected by various methods. First, this can be done by slip casting, i.e. a preferably aqueous solution containing the seed particles is brought into contact with that side of the substrate which is to be coated and, either as a result of applying excess pressure on the side to be coated relative to the side not to be coated, or as a result of a capillary suction exerted by the force, the solution surrounding the seed particles is introduced into the pores while the seed particles, provided that they are larger than the pores of the substrate, accumulate on that side of the substrate which is to be coated. Secondly, the adhesion of the seed particles to the substrate can also be effected by means of a suitable assistant. For example, polymeric quaternary ammonium salts, such as poly-DADMAC (Redifloc®) is suitable for this purpose.

The process step (a) of the novel process comprises the hydrothermal synthesis of a synthesis solution on a substrate material, which, if appropriate, was pretreated as described above for producing a seed layer, by bringing the substrate material into contact with the synthesis solution over a period of from 1 to 100, preferably from 5 to 50, particularly preferably from 10 to 20, hours at from 100 to 250° C., preferably from 140 to 210° C., particularly preferably from 170 to 190° C.

A person skilled in the art will use mixtures known per se as synthesis solution for the hydrothermal synthesis. Said mixtures preferably have the following molar composition:

100 mol of silica,
$5 \times 10^{-5}$ to $2 \times 10^{-1}$, particularly preferably $6 \times 10^{-5}$ to $2 \times 10^{-1}$, mol of alumina $Al_2O_3$,
0 to 2 mol of sodium oxide $Na_2O$,
4 to 11 mol of tetrapropylammonium hydroxide,
0 to 3 mol of tetrapropylammonium bromide,
2 000 to 5 000, particularly preferably 2000 to 3000, mol of water.

100 mol of tetraethyl orthosilicate (TEOS) are used as the Si source, 400 mol of ethanol form and 200 mol of water are consumed.

In the novel process for the production of the membranes, the molar ratio of silicon to aluminum during the hydrothermal synthesis is preferably greater than 120, particularly preferably greater than 200, in particular greater than 300.

As in the case of the seed solution, said tetrapropylammonium salts serve as structure-imparting agents (templates). However, it is possible instead also to use other templates, for example 1,6-hexanediol and piperazine. A detailed description in this context is to be found in: R. Szostak, Handbook of Molecular Sieves, page 521.

A colloidal silica sol, such as Levasil from Bayer, or an organosilicon compound, e.g. tetraethyl orthosilicate (TEOS) is preferably used as the silica source. The aluminum contained in said silicate, a sodium aluminate solution, metallic aluminum, an inorganic aluminum salt or an organoaluminum compound, for example aluminum isopropylate, can preferably serve as the $Al_2O_3$ source. The water used is preferably a water demineralized by means of an ion exchanger, particularly preferably a water demineralized by means of an ion exchanger with at least one subsequent distillation.

The above synthesis solution is preferably prepared in such a way that water, tetrapropylammonium hydroxide, tetrapropylammonium bromide and the aluminum source are premixed and are stirred for, preferably, from 1 to 120, particularly preferably from 5 to 60, minutes and then, preferably, the silica source, in dissolved, colloidal or suspended form, is introduced preferably in the course of from 1 to 100, particularly preferably from 2 to 50, minutes.

The solution is preferably stirred for a further 1 to 200, particularly preferably 5 to 100, minutes and aged for from 1 to 150, particularly preferably from 5 to 50, minutes without stirring.

During the abovementioned steps, the temperature is preferably kept at from 5 to 100° C., particularly preferably from 15 to 40° C.

The synthesis solution thus prepared is then brought into contact with the optionally seeded substrate for from 1 to 100, particularly preferably from 5 to 50, in particular from 10 to 20, hours. During this procedure, the temperature is from 100 to 250° C., particularly preferably from 140 to 210° C., in particular from 170 to 190° C.

The bringing into contact can be effected in various ways. For example, during the synthesis time, the synthesis solution can substantially be left to stand or can be agitated continuously or at regular or irregular intervals over the substrate to be coated, in the same direction or changing directions. A procedure which ensures that the synthesis solution comes into contact predominantly with the surfaces of the substrate which are to be coated and to a lesser extent with the opposite side is advantageous. If, for example in the case of a tubular membrane, an internal coating is desired, it is advantageous to make it more difficult for the synthesis solution to come into contact with the outside of the tube. This can be achieved, on the one hand, by suitably covering the surface(s) to be coated by a removable layer which is difficult for the synthesis solution to penetrate. In the case of the tube to be coated on the inside, this covering layer may be achieved by winding with a tape, for example comprising PTFE, or by means of a suitable brushable polymer solution. On the other hand, access of the synthesis solution to the surface(s) not to be coated can, however, also be made more difficult by filling the pores of the substrate during the synthesis with a medium which restricts or hinders the passage of the synthesis solution through the pores of the substrate. This medium may be, for example, a liquid in which the synthesis solution is only slightly soluble, or is solid which is introduced as a melt into the pores of the substrate and, after the end of the synthesis, is removed by melting or dissolving with a suitable solvent, or a gas, e.g. air or nitrogen, which is present in the space adjacent to the surface(s) not to be coated and at least partly in the pores of the substrate, the pressure of the gas being adjusted so that passage of the synthesis solution from the side to be coated to that side of the substrate which is not to be coated is suppressed.

In a particularly preferred embodiment of the present invention, the synthesis of the separation layer on the substrate material is effected as in the simultaneously filed German Patent Application DE 10 2004 001 975.4 with the title "Production of membranes" of BASF AG (PF 0000055247/WW). In this process, a membrane which contains at least one solid layer on a side of a porous sheet-like substrate which can be shaped into a three-dimensional structure is produced. The production is effected by treating that side of the substrate which is to be coated with a synthesis solution forming a solid layer. In the production of the solid layer on the porous sheet-like substrate, the space which is present behind that side of the porous substrate which is not to be coated is filled with an inert fluid, the pressure and/or the temperature of the fluid being chosen so that contact with the synthesis solution with that side of the porous substrate which is not to be coated is substantially prevented. In particular, the pressure of the fluid during the production of the solid layer is kept at a value which corresponds at least to the pressure of the synthesis solution if the contact angle between synthesis solution and substrate material is less than 90°. If the contact angle between synthesis solution and substrate material is greater than 90°, the pressure during the production of the solid layer is kept in particular at a value which corresponds to not more than the pressure of the synthesis solution. For further information on this procedure, reference is made to the corresponding German Application, which is hereby incorporated by reference.

In a particular embodiment of the novel process, therefore, in the hydrothermal synthesis of the synthesis solution on the substrate, access of the synthesis solution to the surface not to be coated or to the surfaces of the substrate which are not to be coated is substantially prevented by a medium which is present in the pores of the substrate and on the surface not to be coated or the surfaces not to be coated.

It is advantageous to carry out the preparation of the seeds and of the synthesis solution and the hydrothermal synthesis in vessels which can release virtually no aluminum to the solutions. Low-aluminum steels and/or organic polymers, for example PTFE, PFA or polypropylene, or materials which are coated with at least one of said materials on the areas in contact with the solution are suitable for this purpose.

After the synthesis, the membrane produced is washed once or several times with water or an acidic solution in process step (b) in order to remove traces of alkali. The acidic solution may be an aqueous solution of an inorganic or organic acid, for example acetic or formic acid, the acid concentration preferably being from $10^{-5}$ to 1, particularly preferably from $10^{-4}$ to 0.01, mol/l and the duration of the washing operations preferably being from 5 to 120, particularly preferably from 10 to 90, minutes.

Thereafter, drying of the membrane at from 5 to 40° C., particularly preferably from 20 to 30° C., for, preferably, from 1 to 100, particularly preferably from 10 to 30, hours is effected in process step (c), a flowing or stationary gas, for example nitrogen or air, preferably being present over the material to be dried.

In process step (d), a calcination of the membrane at a heating rate of from 0.1 to 1, preferably from 0.3 to 0.7, K/min up to a temperature of from 200 to 600° C., preferably from 350 to 500° C., is effected, residence being effected at the final temperature for from 30 to 500, preferably from 400 to 500, minutes and then cooling being effected at a rate of from 0.1 to 10, preferably at from 0.3 to 1, K/min. During the calcination, an intermediate temperature of, preferably, from 300 to 450° C., particularly preferably from 380 to 420° C., is maintained for a hold time of, preferably, from 100 to 500, particularly preferably from 400 to 450, minutes.

The calcination may be followed by an aftertreatment with a proton-accepting liquid. The proton-accepting liquid is preferably an aqueous solution of one or more substances which act as Brönsted bases, for example ammonia, alkali metal hydroxides, alkali metal carbonates or, particularly preferably, alkali metal bicarbonates. The solutions used are preferably from 0.001 to 1 N, particularly preferably from 0.005 to 0.1 N. This treatment step is preferably carried out for a period of from 10 to 200, particularly preferably from 30 to 100, minutes.

The membrane thus produced can also be subjected to a further treatment step in which, for closing any defects, at least one further layer is applied, for example comprising a metal oxide, preferably silica, or a polymer, preferably a polydialkylsiloxane, particularly preferably polydimethylsiloxane.

The present invention furthermore relates to the composite membranes which can be produced by the novel process.

The present invention furthermore relates to a process for separating olefin-containing mixtures in at least one membrane apparatus, comprising at least one membrane, in which the olefin-containing mixture (feed) flows into the membrane apparatus, is brought into contact with at least one membrane and is separated into a stream (permeate) passing through the membrane and a stream (retentate) not passing through the membrane.

In the novel separation process, a composite membrane as described above or as obtained in the novel process is used.

In the novel process for separating olefins, the membranes are preferably used in modules. In these modules, in each case one of the membranes described is sealed in such a way that the MFI layer separates the feed space and the permeate space from one another. If the membranes are present in the form of tubes or multichannel elements, the sealing in can be effected by means of O-rings comprising elastomers Viton® or Kalrez® or by casting the elements into a polymeric or ceramic potting compound at least one end of the elements and subsequently cutting off the potting compound. Casting of only one element is expedient only in the case of tubular modules in which the feed space is present on the outside of the tube and in which the tubes are closed at the end not sealed in. In the case of tubular membranes or multichannel elements, the jacket space around the tubes preferably has a cylindrical shape.

In the novel process for separating olefins, preferably one or more of modules described are component(s) of a membrane unit. This can be operated in a plurality of ways known per se to a person skilled in the art. An example of these is gas separation in which the feed stream is brought into contact in gaseous form with the membrane. Alternatively, pervaporation is conceivable, the mixture (feed) to be separated being brought into contact in liquid form with the membrane, and the stream (permeate) passing through the membrane being taken off in gaseous form.

The temperature at which the mixture to be separated is brought into contact with the membrane is preferably from 20 to 200° C., particularly preferably from 50 to 150° C.

The pressure on the feed side of the membrane is preferably from 1 to 100, particularly preferably from 1 to 35, bar (abs).

The pressure on the permeate side is preferably from 0.01 to 10, particularly preferably from 1 to 6, bar (abs), the pressure on the retentate side of the membrane generally being higher than that on the permeate side.

The pressure on the permeate side is preferably set by removing the permeate stream by means of a vacuum pump and/or of a compressor and/or by condensing the permeate stream at a temperature which leads to an autogenous pressure of the permeate mixture which corresponds to the desired permeate pressure.

It is also possible to reduce the partial pressure of the permeating components by introducing a sweep gas on the permeate side. Suitable sweep gases are, for example, nitrogen and steam.

In the case of the pervaporation, it may be advantageous to divide the required membrane area over a plurality of apparatuses and, for compensating the heat loss caused by the liquid-gas phase transition, to connect one or more heat exchangers between the membrane apparatuses.

The membrane process can, if appropriate, be carried out in one stage, i.e. both the retentate and the permeate from one membrane apparatus or the combined permeates from a plurality of membrane apparatuses through which the feed flows in succession and/or in parallel leave the membrane unit without further treatment. The membrane process can, however, also be carried out in two or more stages, the permeate from one stage being introduced as feed into the respective subsequent stage and the retentate from this state being mixed with the feed in the first-mentioned stage.

Such arrangements are known per se, cf. Sep. Sci. Technol. 31 (1996), 729 et seq.

Said process is particularly suitable for separating olefin-containing mixtures, preferably for separations of mixtures of linear and branched olefins, e.g. 1-butene/isobutene or other mixtures of isomeric butenes. It can be particularly advantageously used when, for working up an olefin mixture, it is connected upstream of a process in which either a linear olefin, e.g. 1-butene, or a branched olefin, e.g. isobutene, is required.

The examples which follow illustrate the invention.

WORKING EXAMPLES a) Pretreatment of the Substrates

Three porous substrates in tubular form (length 250 mm, external diameter 10 mm, internal diameter 7 mm, pore size on the inside 5 nm for membranes 2 and 3 and 1 nm for membrane 1, for material cf. table, provided with glass solder at the ends) were first coated with seeds (silicalite crystals having a size of from 30 to 100 nm) on the inside by means of slip casting. Thereafter, the tube was heated to 400° C. at a rate of 0.75 K/h maintained at 400° C. for 7 hours and then cooled to room temperature at a rate of 0.75 K/h. Thereafter, the tube was wound with PTFE tape on the outside and placed in a synthesis solution prepared according to the following description.

b) Preparation of the Synthesis Solution

The composition of the synthesis solutions is shown in the table. The source of $SiO_2$, $Al_2O_3$ and $Na_2O$ was the silica sol Levasil® 300/30% (from Kurt Obermeier, Bad Berleburg, Germany) having an $SiO_2/Al_2O_3/Na_2O$ ratio of 90/0.15/1.66. In the case of membrane 1, the $Al_2O_3$ fraction was moreover increased by adding aluminum isopropylate (from Strem Chemicals), which is also the source of $C_3H_7OH$.

Water (purified by means of ion exchange and double distillation), TPAOH (40% strength aqueous solution, from Alfa Aesar), TPABr (from Merck) and, in the case of membrane 1, aluminum isopropylate were introduced into a polypropylene conical flask and stirred at room temperature for 30 minutes. Thereafter, the Levasil was added dropwise with stirring, and aging was then effected at room temperature in the stationary state for 30 minutes.

c) Hydrothermal Synthesis

The syntheses were effected at 180° C. over a duration of 16 hours by placing the cold autoclave containing the synthesis solution in a preheated drying oven. After the synthesis, the Teflon tape was removed.

d) Aftertreatment

The membrane was placed in a measuring cylinder and washed several times with the cleaning solution (cf. table) with stirring. Thereafter, the membranes were allowed to dry for about 20 hours in the room air and then introduced into a through-circulation oven, heated there at a rate of about 0.7 K/h initially to 400° C. and, after a hold time of 400 minutes, at a heating rate of 0.1 K/min to 450° C. and left there for 400 minutes. Cooling to room temperature was then effected at a rate of 0.75 K/h.

e) Permeation Experiments

For the permeation experiments, the membranes were placed in a test module. The sealing of the feed space from the permeate space was achieved by means of a O-ring seal. The O-rings were placed on the vitrified ends of the substrate. The test module was placed in an oven.

Before the measurements, the membranes were evacuated and the feed lines and the oven were preheated to 130° C. The individual gas flows of $H_2$, $N_2$, 1-butene and isobutene were then determined. After each individual gas measurement, the feed space and permeate space were evacuated. The test gas was a 50/50 1-butene/isobutene mixture (from Linde, purity of the gases in each case 99.5%), present in a gas cylinder. The test module was fed therefrom on the feed side. After the test module, the pressure on the feed side was adjusted to 2.5 bar (abs) by means of a back pressure controller. The measurement of the amount of permeate and of the amount of retentate was effected by means of commercially available soap bubble counters. During the permeation measurements, the temperature of the test module was kept at 130° C.

The permeate stream leaving the test module (permeate pressure: about 1 bar (abs)) was passed into the sample loop of a GC-MS apparatus and analyzed there.

In addition to the components of the test mixture, on the one hand the isomerization products cis- and trans-2-butene and on the other hand a plurality of $C_8$-hydrocarbons were found. No $C_8$-hydrocarbons were found in the test gas itself. The concentrations of the 2-butenes in the test gas were <0.1%. The quantitative determination was carried out for the isomeric butene by comparison of the respective ion currents with the signal of 1-butene, and for the $C_8$-hydrocarbons by admixing trans-2-octene as an internal standard.

The results of the measurements are shown in the table, together with the critical properties of the membranes produced and investigated:

|  | Membrane 1 | Membrane 2 | Membrane 3 |
|---|---|---|---|
| Material of the substrate | $TiO_2$ 1 nm (innermost layer) on $Al_2O_3$ | $Al_2O_3$ 5 nm | $TiO_2$ 5 nm |
| Molar ratio in the synthesis solution [1] | 90/10, 41/1, 66/3, 7/2, 3/1, 56/1990 | 90/0, 15/1, 66/3, 7/2 3/0/1990 | as for membrane 2 |
| Washing after hydrothermal synthesis | 4 × 1 h Water | 4 × 1 h dilute FA [2] | as for membrane 2 |
| Permeate concentration (amounts by weight): | | | |
| 1-Butene in the permeate | 79% | 85.6% | 85% |
| 2-Butenes in the permeate | 2% | 0.4% | <0.1% |
| $C_8$-Hydrocarbons in the permeate | 0.5% | 0.1% | 17.5 ppb |

[1] $SiO_2/Al_2O_3/Na_2O/TPAOH/TPABr/C_3H_7OH/H_2O$
[2] Formic acid 0.001 mol/l

The measurements show that the increase in the molar Si/Al ratio is sufficient to lead to a reduction in the catalytic activity of the membrane in the context of olefin isomerization and olefin dimerization, but that this effect is substantially more pronounced in the case of the novel combination of high molar Si/Al ratio and low-aluminum substrate.

We claim:

1. A process for the production of a composite membrane comprising at least one porous substrate and at least one porous separation layer wherein the separation layer contains at least one zeolithe of the MFI type and the molar ratio of silicon to aluminum in the separation layer is greater than 120 and wherein the substrate contains less than 10% by weight of aluminum in elemental or chemically bound form in a zone of at least 100 nm adjacent to the separation layer and the substrate material has an asymmetrical structure, comprising the following process steps:
   (a) hydrothermal synthesis of a synthesis solution, in which the molar ratio of silicon to aluminum is greater than 120, on a substrate by bringing the substrate into contact with the synthesis solution over a period of from 1 to 100 hours at from 100 to 250° C.,
   (b) washing of the membrane resulting from process step (a) with water or an acidic solution for a period of from 5 to 120 minutes,
   (c) drying of the membrane at from 5 to 40° C. over a period of from 1 to 100 hours in the presence of a flowing or stationary gas,
   (d) calcination of the membrane at a heating rate of from 0.1 to 1 K/min to a temperature of 200 to 600° C., residence being effected at the final temperature for from 30 to 500 minutes and then cooling being effected at a rate of 0.1 K/min to 10 K/min.

2. A process according to claim 1, wherein the substrate material used in process step (a) is subjected, before the hydrothermal synthesis, to a seeding step in which a layer of seed particles which at least partly covers that side of the substrate which is to be coated is applied to said side.

3. A process according to claim 1, wherein, in the hydrothermal synthesis of the synthesis solution on the substrate, access of the synthesis solution to a surface not to be coated or to surfaces of the substrate which are not to be coated coated is substantially prevented by a medium which is present in the pores of the substrate and on the surface not to be coated or the surfaces not to be coated.

* * * * *